US010018537B2

(12) United States Patent
Verdier et al.

(10) Patent No.: US 10,018,537 B2
(45) Date of Patent: *Jul. 10, 2018

(54) PORTABLE DEVICE FOR COLLECTING PARTICLES AND MICROORGANISMS

(71) Applicant: Bertin Technologies, Montigny le Bretonneux (FR)

(72) Inventors: Amandine Verdier, Malakoff (FR); Daniel Trouchet, Paris (FR); Julien Charpentier, Puteaux (FR); Bruno Vallayer, Bouc Bel Air (FR)

(73) Assignee: Bertin Technologies, Montigny le Bretonneux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/136,076

(22) Filed: Apr. 22, 2016

(65) Prior Publication Data

US 2016/0238493 A1 Aug. 18, 2016

Related U.S. Application Data

(63) Continuation of application No. 13/881,459, filed as application No. PCT/FR2011/052445 on Oct. 19, 2011, now Pat. No. 9,328,322.

(30) Foreign Application Priority Data

Oct. 27, 2010 (FR) .................................... 10 58870

(51) Int. Cl.
*C12M 1/26* (2006.01)
*A01B 1/06* (2006.01)
(Continued)

(52) U.S. Cl.
CPC .............. *G01N 1/2211* (2013.01); *A62B 7/10* (2013.01); *A62B 18/045* (2013.01); *C12M 1/261* (2013.01);
(Continued)

(58) Field of Classification Search
CPC ......... G01N 1/2273; G01N 2001/2223; G01N 1/2211; G01N 1/24; G01N 33/0011;
(Continued)

(56) References Cited

U.S. PATENT DOCUMENTS 4,350,507 A 9/1982 Greenough et al.
4,430,995 A * 2/1984 Hilton ............... A61M 16/0057
128/204.21
(Continued)

FOREIGN PATENT DOCUMENTS

EP 2 100 637 A1 9/2009
FR 2 855 831 A1 12/2004
FR 2 905 379 A1 3/2008

OTHER PUBLICATIONS

International Search Report and Written Opinion for Application No. PCT/FR2010/052445 dated Dec. 28, 2011.

*Primary Examiner* — Randy Gibson
*Assistant Examiner* — Gedeon M Kidanu
(74) *Attorney, Agent, or Firm* — Alston & Bird LLP

(57) ABSTRACT

A portable device for collecting particles and microorganisms is provided. The device includes a cyclone enclosure for centrifuging air, external air inlet for admitting air into the enclosure, and air outlet connected by a coupling to an air inlet filter of an individual motorized respiratory protection appliance.

21 Claims, 3 Drawing Sheets

(51) Int. Cl.
*A62B 7/10* (2006.01)
*G01N 1/22* (2006.01)
*A62B 18/04* (2006.01)
*G01N 1/24* (2006.01)

(52) U.S. Cl.
CPC ......... *G01N 1/2208* (2013.01); *G01N 1/2273* (2013.01); *G01N 1/24* (2013.01); *G01N 2001/2276* (2013.01)

(58) Field of Classification Search
CPC ................ G01N 1/2205; G01N 1/405; G01N 2001/2217; G01N 2001/245; G01N 30/06; G01N 33/497; A62B 7/10; B01D 39/1676; B01D 45/12; B01D 46/00; B01D 53/0407; B01D 53/0454; Y10S 55/24; Y10S 55/35; Y10S 55/42
USPC .................... 73/28.04, 31.06, 861.42, 863.21
See application file for complete search history.

(56) References Cited

U.S. PATENT DOCUMENTS

| | | | | |
|---|---|---|---|---|
| 4,590,951 A | * | 5/1986 | O'Connor | A62B 18/006 128/201.25 |
| 4,971,052 A | * | 11/1990 | Edwards | F04D 27/004 128/205.12 |
| 5,592,935 A | * | 1/1997 | Elstran | A62B 7/02 128/205.25 |
| 5,861,053 A | | 1/1999 | Noritake et al. | |
| 5,906,203 A | * | 5/1999 | Klockseth | A62B 18/006 128/201.25 |
| 7,452,394 B2 | * | 11/2008 | Vallayer | B01D 45/12 55/337 |
| 8,465,574 B2 | | 6/2013 | Horne | |
| 8,667,959 B2 | * | 3/2014 | Tilley | A62B 18/006 128/201.25 |
| 2006/0144025 A1 | * | 7/2006 | Vallayer | B01D 45/12 55/428 |
| 2006/0254226 A1 | * | 11/2006 | Jeon | A47L 9/1625 55/345 |
| 2007/0163588 A1 | * | 7/2007 | Hebrank | A61L 9/16 128/204.18 |
| 2007/0215159 A1 | * | 9/2007 | Ross | A62B 7/08 128/205.28 |
| 2008/0028940 A1 | * | 2/2008 | Han | B01D 45/16 96/417 |
| 2009/0038645 A1 | * | 2/2009 | Nomura | B08B 3/04 134/18 |
| 2010/0000540 A1 | * | 1/2010 | Pouteau | B03C 3/16 128/205.27 |
| 2010/0089173 A1 | | 4/2010 | Verdier et al. | |
| 2010/0224190 A1 | | 9/2010 | Tilley et al. | |
| 2010/0236012 A1 | | 9/2010 | Horne | |

* cited by examiner

PORTABLE DEVICE FOR COLLECTING PARTICLES AND MICROORGANISMS

CROSS REFERENCE TO RELATED APPLICATIONS

This application is a continuation of U.S. application Ser. No. 13/881,459, filed Aug. 13, 2013, which is a national stage application of International Application No. PCT/FR2011/052445, filed Oct. 19, 2011, which claims priority from French Application No. 10 58870, filed Oct. 27, 2010, the entire contents of which are incorporated herein by reference.

The present invention relates to a portable device for collecting particles and microorganisms present in ambient air, for purposes of identifying and counting such particles and microorganisms.

Such identification and counting are important in numerous fields such as the pharmaceutical industry, the agri-food industry, medical premises, hygiene services, veterinary services, site surveillance, etc; with the dimensions of the particles and microorganisms that are to be collected lying in the range 0.5 micrometers ($\mu$m) to several tens of micrometers.

Devices of this type are known from document fr-a-2 855 831 or from document fr 2 905 379 in the name of the Applicant, which devices comprise a removable centrifuging enclosure containing a collection liquid and associated with air suction means. The enclosure has an air inlet and an air outlet, and it forms a container for transporting a liquid sample containing the collected particles and microorganisms.

Those devices are self-contained, and although they are portable, they are nevertheless relatively bulky. In operation, the flow rate of air passing through the enclosure is relatively large, i.e. greater than 100 liters per minute (L/min). The air flow rate is a function of the application, and in general it is determined so as to take reliable and representative samples in a few minutes.

People who are to move about in a contaminated atmosphere or who are confronted with nuclear, biological, and/or chemical risks are required to wear respiratory protection appliances that may be fitted with filter means for purifying ambient air by filtering it.

Such appliances may be free ventilation appliances, with air passing through the filters solely as a result of the user breathing, or they may be assisted ventilation appliances with the ambient air being sucked in through filters with the help of motorized means.

Known respiratory appliances are not suitable for analyzing the atmosphere in which the users have been moving. When it is desired to perform such an analysis, the user must carry a dedicated collector device, of the type described in the above-mentioned documents fr-a-2 855 831 and fr 2 905 379, and make the device operate in situ, which is not always possible in certain contexts.

A particular object of the invention is to provide a solution to that problem that is simple, effective, and inexpensive.

To this end, the invention provides a portable collector device for collecting particles and microorganisms present in ambient air, the device comprising a cyclone enclosure for centrifuging air, the enclosure being of conical or frusto-conical shape, external air inlet means for admitting air into the enclosure, and air outlet means for discharging air from the enclosure, the device being characterized in that it includes coupling means for coupling the air outlet means of the enclosure to air inlet means of an individual motorized respiratory protection appliance.

The collector device of the invention can thus be associated with a respiratory protection appliance in such a manner as to enable particles and microorganisms to be collected continuously throughout the mission of the user, and throughout the duration for which the respiratory protection appliance is in operation.

Advantageously, the coupling means for coupling to the air outlet of the enclosure comprise connection means for connecting to at least one inlet filter of the respiratory protection appliance.

The connection means may comprise at least one end-piece for engaging on the inlet filter of the appliance.

The collector device may then be fitted to and removed from the filter very easily.

According to another characteristic of the invention, the inside surface of the cyclone enclosure is constituted by or covered in an electrostatic material or a material based on nanofibers for collecting the particles or the microorganisms.

By way of example, this material may be an "electret", which is a dielectric material presenting a quasi permanent state of polarization.

In conventional manner, the external air inlet means lead tangentially into the top portion of the enclosure and the air outlet means lead axially into the top portion of the enclosure.

In a preferred embodiment of the invention, the top portion of the enclosure has a diameter lying in the range 10 millimeters (mm) to 50 mm, and the height or axial dimension of the enclosure lies in the range 10 mm to 100 mm.

The invention also provides an individual motorized respiratory protection appliance including a mask, for being worn by a user, and motorized air feed means, e.g. a turbine, enabling external air to be sucked through at least one filter for retaining the particles or the microorganisms present in the external air, the appliance being characterized in that a collector device of the above specified type is mounted on the filter, upstream therefrom in the external air suction direction.

Advantageously, the air feed means, the filter, and the collector device are dimensioned to supply the user with a continuous flow rate of air that is less than 100 L/min, corresponding to the user's breathing requirements.

Preferably, the appliance is designed to be carried and used for continuous periods of time that may reach approximately 8 hours (h) to 10 h, with particles and microorganisms from external air being collected continuously and while dry inside the cyclone enclosure of the above-mentioned device throughout the duration the respiratory protection appliance is in use.

In a variant, the collector device of the invention can be connected to the air inlet of a motor-driven suction turbine powered by electric batteries, the assembly being designed to be worn by a person and to operate continuously for a duration of several hours, e.g. for about half a day.

The invention also provides a method of collecting and assaying particles and microorganisms present in ambient air, the method being characterized in that, after using the above-specified respiratory protection appliance, it consists in disassembling the cyclone enclosure, in rinsing its inside surface with an appropriate liquid in order to recover the particles and/or the microorganisms collected on said surface, and in analyzing and/or assaying the content of the liquid sample as obtained in this way.

The method may also consist in subjecting the enclosure to ultrasound, after or during rinsing thereof, so as to separate the particles and/or the microorganisms from its inside surface.

The invention can be better understood and other details, characteristics, and advantages of the invention appear on reading the following description made by way of nonlimiting example and with reference to the accompanying drawings, in which.

Figure 1:
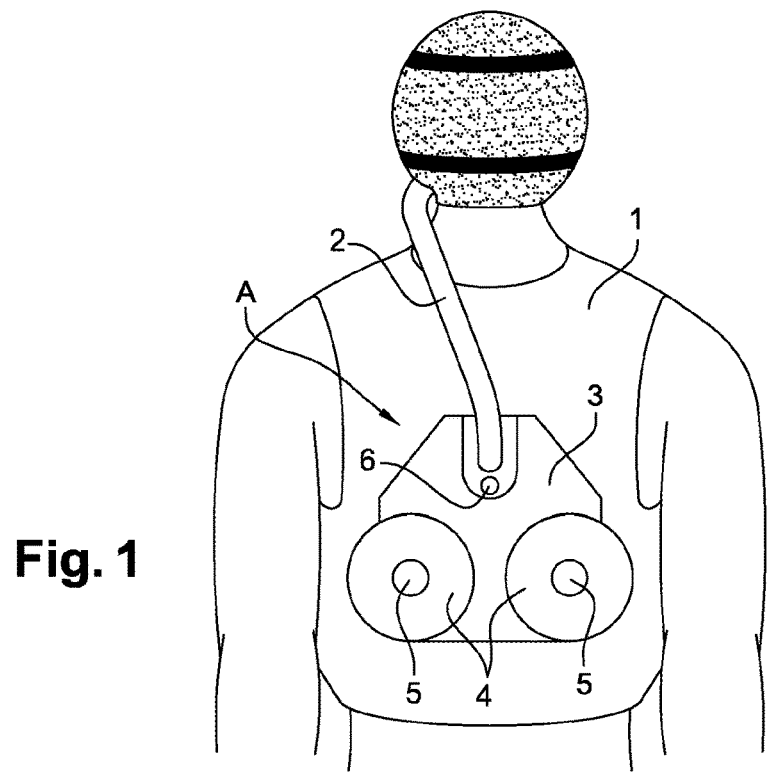
FIG. 1 is a diagrammatic view showing a person wearing a prior art individual motorized appliance for respiratory protection.

FIG. 1 shows a person wearing a jacket 1 having its back fitted with an individual motorized appliance A for respiratory protection that includes a mask (not shown) connected by a pipe 2 to motorized air feed means 3, e.g. to a turbine, enabling outside air to be sucked in through two filters 4 that are to retain particles or microorganisms present in the surrounding atmosphere.

Each filter 4 is generally cylindrical in shape and includes a central air inlet 5 situated in its rear face.

The appliance A is fitted with control means 6 enabling the motorized air feed means 3 to be switched on or off, and enabling the flow rate of air fed to the mask to be adjusted.

Figure 2:
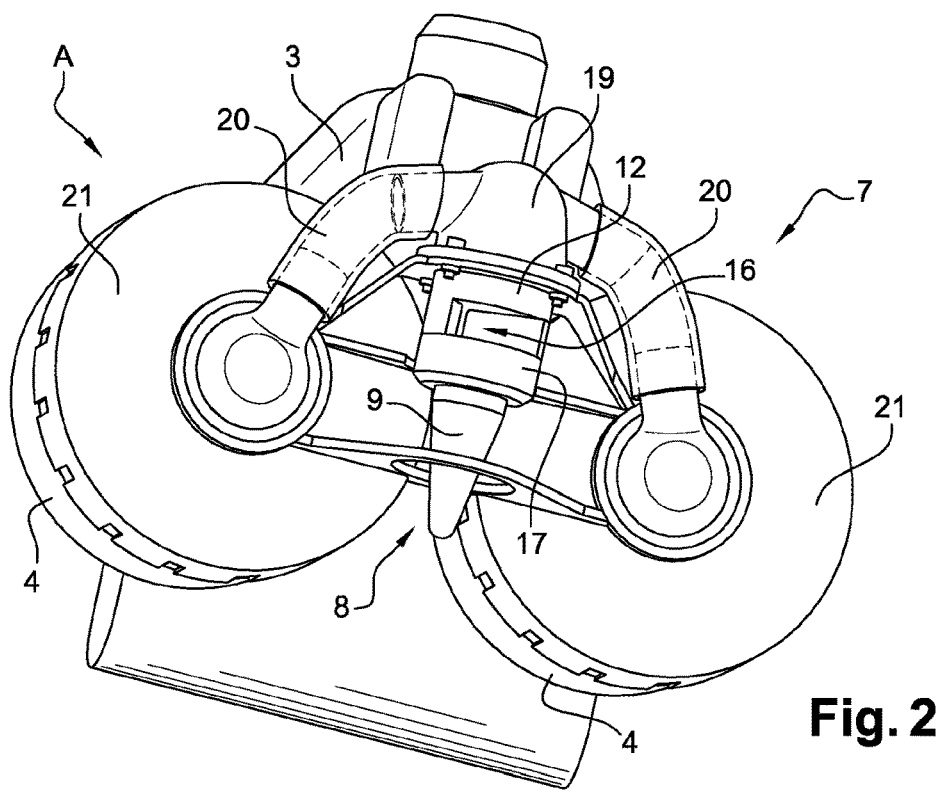
FIG. 2 is a perspective view of a respiratory protection appliance of the invention.
Figure 3:
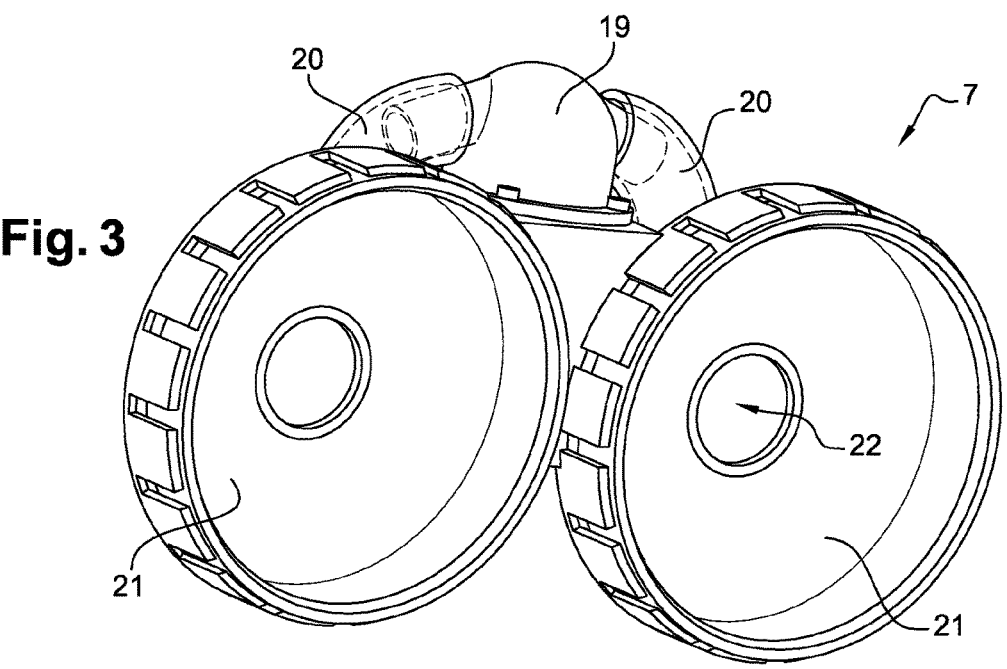
FIG. 3 is a perspective view of a collector device of the invention.

As shown in FIG. 2, the invention proposes fitting such an appliance with a collector or device 7 for collecting particles and microorganisms that are present in ambient air.

Figure 4:
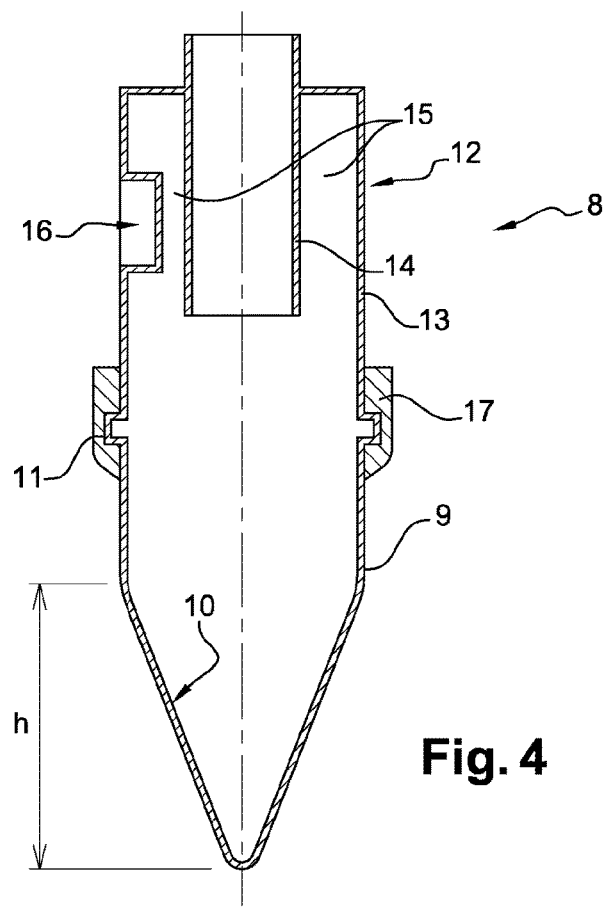
FIG. 4 is an axial section view of a cyclonic enclosure for centrifuging air.
Figure 5:
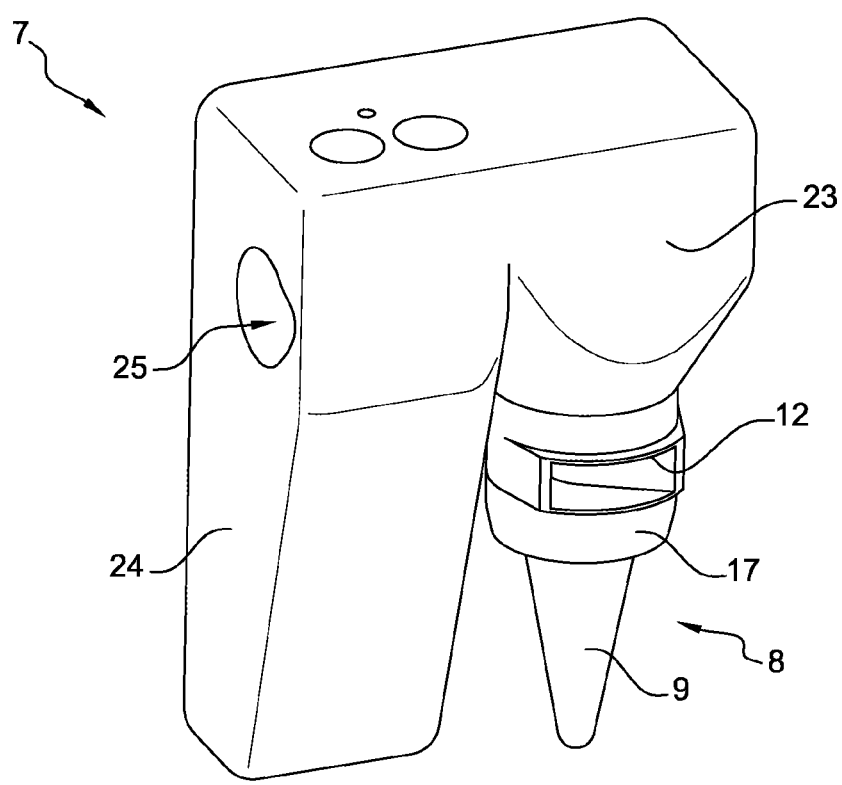
FIG. 5 is a perspective view of a variant embodiment of the invention.

The device 7 comprises a cyclone enclosure 8 for centrifuging air, which enclosure is of conical or frustoconical shape, and its structure can be seen more clearly in FIG. 4.

In its bottom portion, the enclosure 8 is defined by a first part 9 of generally frustoconical or conical shape with an inside surface 10 that is covered in an electrostatic material, e.g. a material of the "electret" type, or a material based on nanofibers, for the purpose of collecting particles or microorganisms. The top diameter of the first part 9 lies in the range 10 mm to 50 mm, and its height h lies in the range 10 mm to 100 mm. The top end of the first part 9 is provided with an annular rim 11 extending radially outwards.

In its top portion, the enclosure 8 is also defined by a second part 12 on top of the first, comprising a cylindrical outer wall 13 and an axial tube 14 co-operating with the outer wall to define an annular air inlet channel 15 leading into the enclosure. The outer wall 13 includes at least one opening 16 leading tangentially into the annular channel 15, so as to form an air inlet into the top portion of the enclosure 8. The bottom end of the second part 12 is provided with an external thread.

The two parts 9 and 12 are fastened together by means of a ring 17 that is mounted on the rim 11 of the first part 9 by crimping or by snap fastening and that is screwed onto the thread of the second part 12.

The axial tube 14 forms an air outlet leading at its bottom end into the enclosure, and connected at its top end to a coupling that can be seen in FIGS. 2 and 3. This coupling 19 is generally T-shaped, with one branch connected to the air outlet 14 of the enclosure 8 and with its other two branches connected to the two filters 4 via bent pipes 20 and assembly endpieces 21. The coupling 19 is fastened, e.g. by screw fastening, to the second part 12 of the cyclone enclosure 8.

The endpieces 21 are cylindrical and form bells that can be engaged directly on the filters 4. More particularly, each endpiece 21 may be made of an elastomer material and may include a central air outlet 22 (FIG. 3) situated in register with the central air inlet 5 of a respective filter 4.

During operation of the respiratory appliance A, the air as sucked in by the motorized means 3 enters via the inlet 16 of the cyclone enclosure 8 and swirls within the enclosure so that the particles and microorganisms present in the ambient air are centrifuged against the electrostatic material or against the material based on nanofibers covering the inside surface 10 of the part 9.

Unlike the above-mentioned prior art, the enclosure 8 operates while dry, i.e. without any liquid being contained in or injected into the enclosure.

In a variant, even though it is not as effective, collection may also be performed in an enclosure 8 that does not have electrostatic material on its inside surface 10.

The air then leaves the enclosure via the outlet 14, passes along the pipes 20, and then through the filters 4 for in order to be purified before reaching the mask. The air flow rate necessary for proper ventilation of the user is less than 100 L/min, even when the user is exerting relatively intense physical effort. The motorized feed means 3 and the cyclone enclosure 8 are of the dimensions that make such a flow rate possible.

After the user has completed a mission, the user stops the motorized feed means 3 of the respiratory protection appliance, and the enclosure 8 can be disassembled. The first part 9 is rinsed using an appropriate liquid in order to recover the particles and/or the microorganisms collected on the inside surface 10 in the form of a liquid sample that can be analyzed and/or assayed using conventional techniques. In this way, the particles or the microorganisms present in the sample can be identified and counted.

In order to improve separation of the particles or the microorganisms, the first part 9 may be subjected to ultrasound, after or during rinsing.

The invention enables particles or microorganisms to be collected continuously and effectively throughout a mission that may have a duration of as long as 10 h.

The contact or device 7, and more particularly the cyclone enclosure 8 may be designed in such a manner as to enable the respiratory protection appliance 2 to operate even in the event of the motorized feed means 3 stopping, merely by the wearer breathing in air. The head losses created by the collector device 7 must therefore be a small enough to make that possible. Otherwise, the collector device 7 of the invention may be fitted with quick disconnection means enabling ambient air to be breathed directly through the filters 4, without passing via the cyclone enclosure 8. The filters 4 are designed to generate head losses that are small enough to enable the appliance 2 to operate in the event of the motorized feed means 3 failing.

FIG. 5 shows a variant embodiment of a device 7 for collecting particles and microorganisms. In this device 7, the air outlet from the enclosure 8 is connected to the air inlet of a suction turbine having an electric motor that is received in a housing 23 and that is powered by batteries that are themselves received in a housing 24. The housings 23 and 24 may be contiguous or they may be spaced apart from each other. The air outlet from the turbine leads to the outside at 25, in the top portion of the housing 24.

The device 7 is designed to be worn by a person and to operate continuously for a duration of several hours.

The invention claimed is:

1. A portable collector device for collecting particles and microorganisms present in ambient air, the device comprising
   a cyclone enclosure for centrifuging air, the enclosure including a wall defining an interior space of the enclosure, a top portion and a bottom portion that is detachable from the top portion, said bottom portion having an inner surface for collecting one or more of microorganisms and particles,
   an opening formed in said wall of the top portion of the enclosure, the opening defining an external air inlet for admitting air into the interior space of the enclosure, wherein air admitted into the interior space is centrifuged against the inner surface,
   an air outlet for discharging air from the enclosure, and a coupling member for coupling the air outlet of the enclosure to an air inlet of an individual motorized respiratory protection appliance, wherein the coupling member comprises a first tubular branch connected to the air outlet, and at least a second tubular branch configured to be connected to an inlet filter of the individual motorized respiratory protection appliance.

2. A device according to claim 1, wherein the inside surface of the bottom portion is constituted by or covered in an electrostatic material or a material based on nanofibers for collecting the particles or the microorganisms.

3. A device according to claim 1, wherein the top portion of the enclosure has a diameter lying in the range 10 mm to 50 mm.

4. An individual motorized respiratory protection appliance including a mask, for being worn by a user, and motorized air feed system, enabling external air to be sucked through at least one filter for retaining the particles or the microorganisms present in the external air, wherein the appliance includes that a collector device according to claim 1 is mounted on the filter, upstream therefrom in the external air suction direction.

5. The portable collector device of claim 1, wherein the top and bottom portions are joined to each other with a ring.

6. The portable collector device of claim 1, wherein the air outlet comprises an axial tube that extends into the top portion of the enclosure and defines an annular air inlet channel between an inner surface of the enclosure and an outer surface of the axial tube.

7. The portable collector device of claim 1, wherein the bottom portion of the enclosure has a frustoconical or conical shape.

8. A device according to claim 1, wherein the coupling member for coupling to the air outlet of the enclosure comprise connection member for connecting to said inlet filter of the respiratory protection appliance.

9. A device according to claim 8, wherein the connection member comprise at least one endpiece for engaging on the inlet filter of the appliance.

10. A device according to claim 1, wherein the coupling member comprises a third tubular branch, and wherein the second and third tubular branches are each configured to be connected to a filter of the individual motorized respiratory protection appliance.

11. A device according to claim 10, wherein the coupling member has a T-shape.

12. A device according to claim 1, wherein the external air inlet lead tangentially into the top portion of the enclosure and the air outlet lead axially into the top portion of the enclosure.

13. A device according to claim 12, wherein the height or axial dimension of the enclosure lies in the range 10 mm to 100 mm.

14. An appliance according to claim 13, wherein the air feed system, the filter, and the collector device are dimensioned to supply the user with a continuous flow rate of air that is less than 100 L/min.

15. A device according to claim 1, wherein the air outlet of the enclosure can also be connected to the air inlet of a motor-driven suction turbine powered by batteries, the assembly being designed to be worn by a person and to operate continuously for a duration of several hours.

16. An appliance according to claim 15, wherein the appliance is configured to be carried and used for continuous periods of time that may reach approximately 8 h to 10 h, and that particles and microorganisms from external air are collected continuously and while dry inside the cyclone enclosure of, the above-mentioned device throughout the duration the respiratory protection appliance is in use.

17. A method of collecting and assaying particles and microorganisms present in ambient air, wherein after using the respiratory protection appliance according to claim 15, the method comprises disassembling the cyclone enclosure, in rinsing an inside surface with an appropriate liquid in order to recover the particles and/or the microorganisms collected on said surface, and in analyzing and/or assaying the content of the sample as produced in this way.

18. A method according to claim 16, wherein the method further includes subjecting the enclosure to ultrasound, after or during rinsing thereof, so as to separate the particles and/or the microorganisms from its inside surface.

19. A portable collector device for collecting particles and microorganisms present in ambient air, the device comprising
   a cyclone enclosure for centrifuging air, the enclosure including:
      a wall defining an interior space of the enclosure;
      an external air inlet for admitting air into said interior space of the enclosure, wherein air admitted into the interior space is centrifuged within the interior space,
      an air outlet for discharging air from the enclosure, the air outlet comprising an axial tube that extends into the top portion of the enclosure and defines an annular air inlet channel between an inner surface of the enclosure and an outer surface of the axial tube, wherein the external air inlet leads tangentially into the annular air inlet channel, and
   a coupling member for coupling the air outlet of the enclosure to an air inlet of an individual motorized respiratory protection appliance, wherein the coupling member comprises a first tubular branch connected to the air outlet, and at least a second tubular branch having a bell-shaped endpiece that is configured to be connected to an inlet filter of the individual motorized respiratory protection appliance.

20. The portable collector device of claim 19, wherein the endpiece comprises an elastomer material.

21. The portable collector device of claim 19, further comprising a third tubular branch having a bell-shaped endpiece, wherein said endpieces of the second and third tubular branches are each configured to be connected to a filter of the individual motorized respiratory protection appliance.

* * * * *

UNITED STATES PATENT AND TRADEMARK OFFICE
CERTIFICATE OF CORRECTION

PATENT NO. : 10,018,537 B2
APPLICATION NO. : 15/136076
DATED : July 10, 2018
INVENTOR(S) : Verdier et al.

It is certified that error appears in the above-identified patent and that said Letters Patent is hereby corrected as shown below:

In the Claims

Column 6,
Line 18, "enclosure of, the" should read --enclosure of the--.

Signed and Sealed this
Eleventh Day of June, 2019

Andrei Iancu
*Director of the United States Patent and Trademark Office*